(12) United States Patent
Lovchik et al.

(10) Patent No.: US 11,458,467 B2
(45) Date of Patent: Oct. 4, 2022

(54) STRUCTURES TO DEFINE FLOW CONFINEMENT SHAPE AND CONFINEMENT STABILITY WITH UNIFORM ASPIRATION

(71) Applicant: BIO-RAD LABORATORIES, INC., Hercules, CA (US)

(72) Inventors: Robert Dean Lovchik, Schoenenberg (CH); Anna Fomitcheva Khartchenko, Zurich (CH); Govind Kaigala, Rueschlikon (CH); Iago Pereiro Pereiro, Zurich (CH)

(73) Assignee: Bio-Rad Laboratories Inc., Hercules, CA (US)

( * ) Notice: Subject to any disclaimer, the term of this patent is extended or adjusted under 35 U.S.C. 154(b) by 107 days.

(21) Appl. No.: 16/532,766

(22) Filed: Aug. 6, 2019

(65) Prior Publication Data

US 2021/0039083 A1 Feb. 11, 2021

(51) Int. Cl.
*B01L 3/02* (2006.01)
*G01N 33/543* (2006.01)
*B01L 3/00* (2006.01)

(52) U.S. Cl.
CPC ....... *B01L 3/0241* (2013.01); *B01L 3/502707* (2013.01); *G01N 33/54306* (2013.01); *B01L 2400/0487* (2013.01)

(58) Field of Classification Search
CPC ............. B01L 3/0241; B01L 3/502707; B01L 2400/0487; B01L 2300/0832; B01L 2200/0668; B01L 3/502761; B01L 2400/0463; B01L 2200/0684; B01L 2300/161; G01N 33/54306
See application file for complete search history.

(56) References Cited

U.S. PATENT DOCUMENTS 9,625,454 B2 4/2017 Strey et al.
9,839,932 B2 12/2017 Uchiyama et al.
(Continued)

FOREIGN PATENT DOCUMENTS

DE 102013207232 A1 10/2014
EP 3162441 A1 5/2017
WO 2015132686 A1 9/2015
WO 2016128543 A1 8/2016
WO 2017187284 A1 11/2017

OTHER PUBLICATIONS

Lovchik et al., "Structures on Microfluidic Devices to Control Sedimentation", U.S. Appl. No. 16/532,798, filed Aug. 6, 2019.
(Continued)

*Primary Examiner* — Jennifer Wecker
*Assistant Examiner* — Oyeleye Alexander Alabi
(74) *Attorney, Agent, or Firm* — Kilpatrick Townsend & Stockton LLP

(57) ABSTRACT

A microfluidic probe head is provided. The microfluidic probe head comprises a processing surface. The processing surface has a first and second aperture and a fluid injection channel, which leads to the first aperture. The microfluidic probe head comprises also a first fluid aspiration channel which leads to the second aperture. Thereby, the second aperture forms a slot in the processing surface. Furthermore, a microfluidic probe may be provided comprising the microfluidic probe head.

20 Claims, 8 Drawing Sheets

(56) References Cited

U.S. PATENT DOCUMENTS

| | | |
|---|---|---|
| 2012/0048391 A1* | 3/2012 | Delamarche ......... B01J 19/0046 |
| | | 137/15.01 |
| 2013/0333761 A1 | 12/2013 | Delamarche et al. |
| 2015/0209783 A1 | 7/2015 | Ingber et al. |
| 2016/0243549 A1* | 8/2016 | Autebert ............... B01L 3/0262 |
| 2017/0059590 A1 | 3/2017 | McPeak et al. |
| 2017/0121663 A1 | 5/2017 | Hinojosa et al. |
| 2018/0117588 A1 | 5/2018 | Ingber et al. |
| 2018/0200677 A1 | 7/2018 | Lee et al. |
| 2018/0318831 A1 | 11/2018 | Kaigala et al. |
| 2018/0318832 A1 | 11/2018 | Kaigala et al. |
| 2019/0018034 A1 | 1/2019 | Kaigala et al. |

OTHER PUBLICATIONS

Kaigala et al., "Prevention and Bubble Removal From Microfluidic Devices", U.S. Appl. No. 16/532,825, filed Aug. 6, 2019.

List of IBM Patents or Patent Applications Treated as Related, Dated Aug. 6, 2019, 2 pages.

Rousset et al., "Simulation-assisted design of microfluidic sample traps for optimal trapping and culture of non adherent single cells, tissues, and spheroids", Scientific Reports, Published Online: Mar. 21, 2017, DOI:10.1038/s41598-017-00229-1, 12 pages.

International Search Report and Written Opinion dated Nov. 17, 2020 in International Patent Application No. PCT/US2020/045118. 10 pages.

International Preliminary Report on Patentability dated Feb. 17, 2022 in International Patent Application No. PCT/US2020/045118. 7 pages.

* cited by examiner

STRUCTURES TO DEFINE FLOW CONFINEMENT SHAPE AND CONFINEMENT STABILITY WITH UNIFORM ASPIRATION

BACKGROUND

The present disclosure relates generally to a microfluidic probe head, and to a microfluidic probe.

A microfluidic probe is a non-contact microfluidic system combining concepts of hydrodynamic flow confinement (HFC) and scanning probes for yielding a dynamic microfluidic device which may enable the need for performing analyses within closed conduits. It operates under the well-known Hele-Shaw cell approximation, wherein a quasi-2D Stokes flow is generated between two parallel generally flat surfaces—i.e., plates—separated by an arbitrarily small gap working in a microfluidic dipole and microfluidic quadrupole configuration. Generally, the method may be used for applications such as patterning protein arrays on flat services, mammalian cell stimulations and manipulations, localized perfusion of tissue slices as well as generating floating concentration gradients. Microfluidic probes have been proposed as a tissue lithography tool, and may allow prospective studies of formalin-fixed, paraffin-embedded tissue sections. The technique has also been used in the microfluidic quadrupole configuration, as a tool for advanced cell chemotaxis studies, wherein it may allow studying cellular dynamics during migration in response to moving concentration gradients.

Hence, microfluidic probes (MFP) create hydrodynamic flow confinements with aligned aspiration and injection channels, resulting in tear drop shapes. Vertical MFPs with one aspiration and one injection channel have structures etched on a single surface, leading to aligned apertures for flow confinements. Such a shape can be limiting for certain applications; for example, when large areas need to be processed in a given time or when the objective is to pattern a surface with a user-defined geometry. In order to obtain more adaptable shapes, horizontal MFPs may be fabricated with multiple apertures distributed on a plane for more flexible flow confinement shapes. An increase in shape complexity requires a higher number of apertures and capillary connections. Multiple tear drop-shaped confinements can be combined to create composite geometries.

SUMMARY

According to an embodiment, a microfluidic probe head is provided. The microfluidic probe head comprises a processing surface. The processing surface has a first and second aperture. The microfluidic probe head comprises a fluid injection channel. The fluid injection channel leads to the first aperture. The microfluidic probe head comprises a first fluid aspiration channel. The first fluid aspiration channel leads to the second aperture. The second aperture forms a slot in the processing surface.

According to another embodiment, a microfluidic probe is provided. The microfluidic probe comprises the microfluidic probe head of the embodiment described above.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Embodiments are described, by way of example only, and with reference to the following drawings.

DETAILED DESCRIPTION

Figure 1:
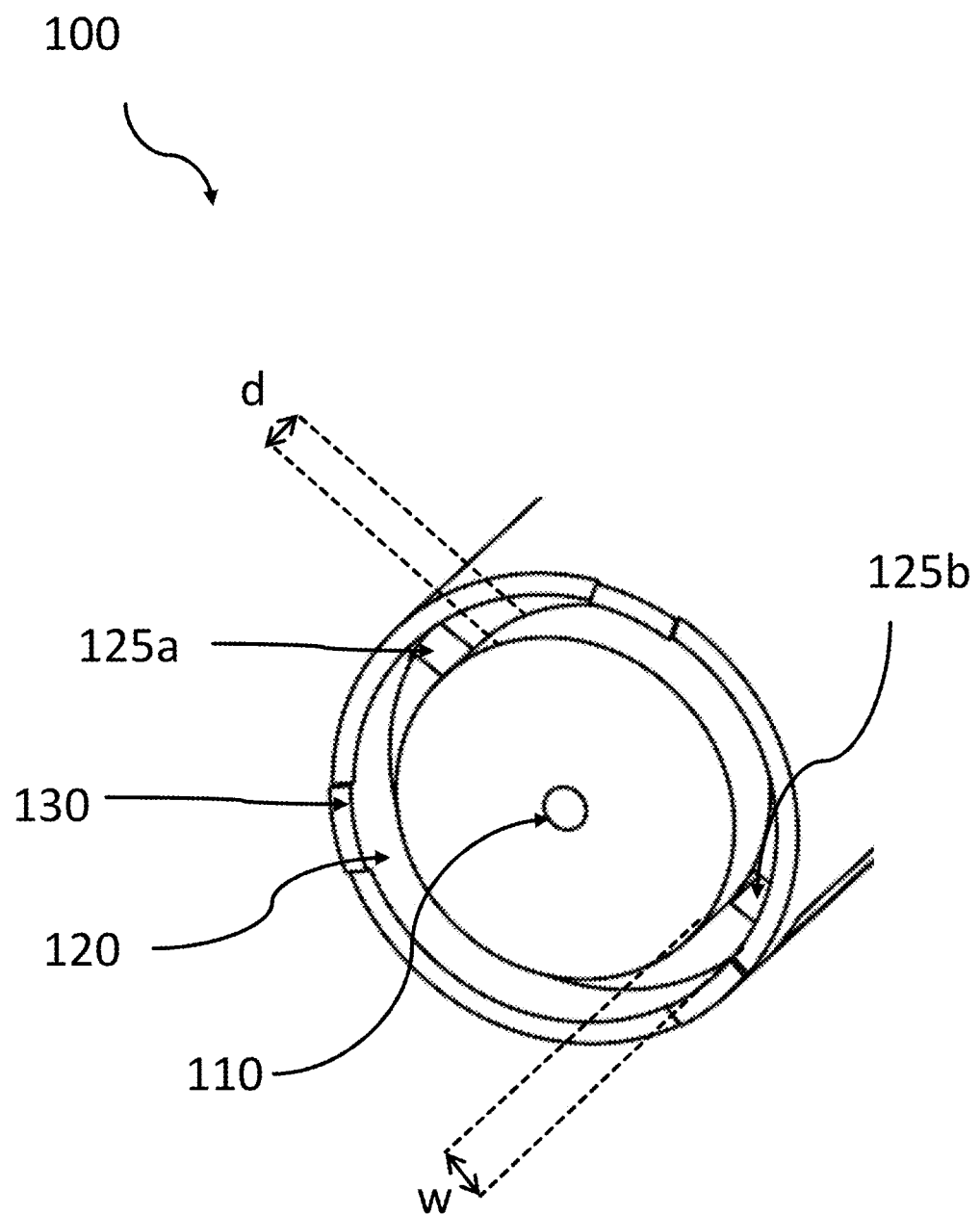
FIG. 1 shows a schematic illustration of an embodiment of a microfluidic probe head.

In the context of this description, the following conventions, terms and/or expressions may be used:

The term 'microfluidic probe head' may denote a mobile scanning probe having, for example a circular, elliptic or otherwise adequately formed processing portion with injection and aspiration opening for supplying and disposal fluids for processing surfaces and objects by scanning across them with the microfluidic probe head.

The term 'processing surface' may denote the part of the microfluidic processing head which comes in contact with the liquids between the microfluidic probe head and the surface to be processed. The processing surface may preferably be round. However, other geometries are possible (e.g., ellipse, squared, etc.).

The term 'first aperture' may denote an opening which defines the end of an injection channel or an entrance from the injection channel to the processing surface.

The term 'second aperture' may denote a slot and simultaneously the beginning of the first/second aspiration channel(s) or entrance from the processing surface to the first/second aspiration channel(s).

The term 'fluid injection channel' may denote the channel used for injecting a fluid like a liquid or a gas onto the processing surface.

The term 'first fluid aspiration channel' may denote the aspiration channel used for receiving the injected fluid from the processing surface.

The term 'point-wise symmetric' may denote that the first aperture may be the central point or "origin" about which the second aperture is symmetrical, in particular has point symmetry.

The term 'axis-symmetrically' may denote that when the shape of the second aperture is folded in half along the axis of symmetry, for example through the first aperture (the "origin"), then the two halves match up.

The term 'at least two protrusions' may denote spacers. The spacers may be arranged and adapted to define a space between the processing surface and the surface to be processed. The spacers may define a space between 10 μm up to 2 mm.

The term 'outer dimension' may denote a border of the processing surface or the microfluidic probe head.

The term 'microfluidic probe' may denote a device used for processing samples in closed micro-channels by hydrodynamically confining liquids that performed chemistries on surfaces. In particular, the microfluidic probe may be a vertical microfluidic probe, herein. The term "vertical" may be defined by the use of the microfluidic probe with respect to gravity.

The fluid injection channel may be a liquid or gaseous injection channel and it may be adapted to inject fluid on the processing surface. Additionally, the first/second/third fluid aspiration channel may be a liquid or gaseous aspiration channel and they may be adapted to receive the fluid from the processing surface.

The proposed microfluidic probe head may offer multiple advantages and technical effects:

Firstly, flow confinements may have a reduced lack of stability to sustain long periods of operation or the presence of disruptive elements (e.g., debris, bubbles). Robust interfaces may be ensured between confined and immersion liquids. Also, intricate internal channel structures to divide the flow evenly among multiple apertures may be avoided.

In the form of 3D printed microfluidic probe heads, they may offer more flexibility and simultaneously have the required resolution. Specific aperture channels clogging may be avoided, and the shape of the flow confinement may be upheld.

A uniform aspiration of a circular groove may ensure that the flow distribution in the inside confinement area is perfectly radial with an equal flow intensity in all directions. The flow velocity distribution in a flow confinement formed by an aspiration ring may be adapted according to requirements and may be homogeneous, so that the mass transport may be easy to predict and control.

Additionally, the grooves may be more easily manufactured than individual aspirations, and the stability of flow confinement at different heights between MFP and the surface to be processed may be ensured.

Even if the surface of the probe is not perfectly parallel to a substrate (i.e., surface to be processed), the confinement may be upheld. If the microfluidic probe is tilted, the resistance may not effectively increase, and the apertures may still work.

Also, 3D printing of the microfluidic probe head may allow the fabrication of such structures in more convenient ways using existing techniques.

Because it may create very effective hydrodynamic walls, aspiration grooves may be used to remove material from a surface (particularly non-specifically bound particles/molecules). The material may then be collected through high shear stress/flow, and the enclosed groove geometry may help in preventing material from escaping outside the scanning path.

Because flow enters the groove from two opposite directions (inside and outside confinement area) any large particles that cannot be aspirated will be collected below the groove area and displaced with the movement of the scanning probe. They can be discarded in any area of the surface that is not active/processed.

The microfluidic probe, or the microfluidic head in particular, may be filled with liquid—known as priming—before productive use. Thus, it may be ensured that no remaining air pockets may exist before an operation start.

The groove may be used for the confinement of gases on surfaces, surrounded by an immersion liquid. The groove may also act as a bubble collector: any bubble resulting from the fluid flow will enter the groove and float to its ceiling, without entering the aspiration channel Thereby, clogging and instability issues may be avoided. For example, as long as most of a volume of the groove is not filled with air, aspiration properties of the aspiration channel(s) may be maintained.

Also, besides stabilizing, the ring structure of the aperture may ensure that the gas-liquid interface follows the movement of the probe as it scans the surface.

In the following, additional embodiments are described:

According to an embodiment of the microfluidic probe head, the second aperture is formed around the first aperture. The second aperture is formed as a closed shape aperture, a single slot and/or as a slot having no end (i.e., a closed loop form), e.g., a groove encircling the first aperture in a distance. This may help to ensure regular aspiration of the injected fluid.

According to an embodiment of the microfluidic probe head, the second aperture is formed apart from the first aperture. This may ensure sufficient provision of fluid on the processing surface.

According to an embodiment of the microfluidic probe head, the first aperture is arranged at the center of the processing surface. The first aperture is arranged in the middle of the processing surface. For example, the first aperture is arranged at less than 60% of a radius of the processing surface. Also, this may help to ensure uniform distribution of the injected fluid on the processing surface.

According to an embodiment of the microfluidic probe head, the second aperture is defined by a first dimension and a second dimension. Thus, the microfluidic probe head is adjustable to different fluidic situations (hydrophilicity/hydrophobicity of the material).

According to an embodiment of the microfluidic probe head, the second aperture is point-wise symmetric around the first aperture. This may help to ensure a point-symmetric distribution of the injected fluid on the processing surface.

According to an embodiment of the microfluidic probe head, the second aperture is axis-symmetrically to an axis running through the first aperture. This may help to ensure an axis-symmetric distribution of the injected fluid on the processing surface.

According to an embodiment of the microfluidic probe head, the second aperture is a circular-shaped slot, rectangular-shaped slot or a triangular-shaped slot. These slots are arranged around the first aperture to ensure a uniform distribution of injected fluid over the processing surface.

According to an embodiment of the microfluidic probe head, the first dimension is a depth of the slot, and the second dimension is a width of the slot.

According to certain embodiments, the depth and/or the width of the slot varies along the slot. In other embodiments, the depth and/or the width is uniform along the slot. This may provide effective hydrodynamic walls.

According to an embodiment of the microfluidic probe head, the first dimension has a size larger than three times the second dimension. This may help to ensure uniformity when using one aspiration channel.

According to an embodiment of the microfluidic probe head, the microfluidic probe head further comprises a second aspiration channel leading to the second aperture. The first dimension has a size between three times the second dimension and twice the second dimension. This may help to ensure uniformity when using two aspiration channels.

According to an embodiment of the microfluidic probe head, the microfluidic probe head further comprises a third aspiration channel. The first dimension has a size between the second dimension and twice the second dimension. This may help to ensure uniformity when using three or four aspiration channels.

According to an embodiment of the microfluidic probe head, at least two out of the first, second and third aspiration channels are point-wise symmetrically arranged with respect to the fluid injection channel. This may also help to ensure uniformity of the fluid flow.

According to an embodiment of the microfluidic probe head, at least one of the first aspiration channel, the second aspiration channel and the third aspiration channel are at a bottom of the second aperture. Additionally, at least one of the fluid injection channels, the first aspiration channel, the second aspiration channel and the third aspiration channel are round channels. This may help to ensure a good drain of the injected liquid.

According to an embodiment of the microfluidic probe head, the fluid injection channel begins at the processing surface. In this context, the first aperture defines a recess in the processing surface, and the fluid injections channel begins (anywhere) in the recess.

According to an embodiment of the microfluidic probe head, respective diameters of the first aspiration channel, the second aspiration channel and the third aspiration channel are at least substantially the same.

According to an embodiment of the microfluidic probe head, a respective diameter of the fluid injection channel is smaller than a sum of respective diameters of the first aspiration channel, the second aspiration channel and/or the third aspiration channel. This may help to ensure sufficient distribution of the injected liquid on the processing surface.

According to an embodiment of the microfluidic probe head, the microfluidic probe head further comprises at least two protrusions at an edge of the processing surface. The at least two protrusions are adapted and arranged to provide a predetermined distance from a surface on which the microfluidic head is applied. The predetermined distance is in a range between 10 μm and 2 mm. For example, the predetermined distance may be larger than 25 μm (or 50 μm or 100 μm or 150 μm or 200 μm or 250 μm or 300 μm or 350 μm or 400 μm or 450 μm or 500 μm). For example, the predetermined distance may be smaller than 2 mm (or 1.75 mm or 1.5 mm or 1.25 mm or 1.0 mm or 0.75 mm).

According to an embodiment of the microfluidic probe head, the at least two protrusions define at least part of an outer dimension of the processing surface. The at least two protrusions are regularly displaced from each other such that they are positioned symmetrically in respect to a point (or line) of symmetry) of the microfluidic probe head.

Thus, in certain embodiments, the protrusions do not completely delimit an area of the processing surface.

In the following, a detailed description of the figures will be given. All instructions in the figures are schematic. Firstly, a block diagram of an embodiment of the microfluidic probe head is given. Afterwards, further embodiments, as well as embodiments of the microfluidic probe, will be described.

FIG. 1 shows a schematic illustration of a microfluidic probe head 100 seen from a direction that would be vis-a-vis a surface to be investigated (i.e., a bottom view). The microfluidic probe head 100 comprises a first aperture 110 from which an injection channel extends into the microfluidic probe head 100. Further, the microfluidic probe head 100 comprises a second aperture 120 in the form of a ring-shaped slot. The second aperture 120 comprises aspiration channels 125a, 125b. In FIG. 1, two aspiration channels 125a and 125b are shown. However, there may also be a single aspiration channel 125a or multiple aspiration channels 125a, 125b starting at the second aperture 120. Further, the microfluidic probe head 100 comprises protrusions 130. The protrusions in FIG. 1 are arranged in a specific distance from each other and may be in the form of spacers. The spacers define a distance from the surface to be processed by the processing surface defined as the surface at one side of the microfluidic probe head 100. The surface to be processed may be in the form of a specific substrate. A fluid may be guided through the injection channel onto the processing surface via the first aperture 110. Due to the amount of fluid, the fluid tends to be collected in the second aperture 120 and be distributed uniformly over the processing surface. The so collected fluid may then be transported through the aspiration channels 125a, 125b, in FIG. 1 through the two aspiration channels 125a and 125b. As shown in the figures, the protrusions 130 do not seem to have a height at all. However, this circumstance is given by the shown perspective and the low height (e.g., of about 25 μm or below) of the protrusions in comparison to the other elements of the microfluidic probe head 100.

A circular flow confinement can be obtained with an enclosed groove (second aperture 120) with complete radial symmetry, as shown in FIG. 1. To provide a uniform aspiration in the whole second aperture 120 (for example named aspiration ring or groove) with an equivalent aspiration velocity, the groove 120 may have a sufficient depth d in dependence of a given width w. The fewer the number of aspiration channels, the deeper the groove may be. Geometrical rules may be given as follows:

if $d>3*w$ → 1 aspiration channels;
if $3*w>d>2*w$ → 2 aspiration channels; and
if $w>d>2*w$ → 3 or 4 aspiration channels.

For example, the circular groove 120 may have a radius of 2.5 mm and w=0.5 mm. In this case, a groove depth d of 1.5 mm may be used to obtain a uniform aspiration with a single aspiration. With a shallower 1 mm groove depth d, two mirrored aspiration channels at the bottom of the groove 120 may be used to obtain a uniform aspiration. In the case of one single aspiration channel, aspiration takes place in the full circle but it is not uniform (higher close to the aperture). In addition, the depth of the groove 120 may be uniform or non-uniform.

The groove 120 can be fabricated in any solid material, as long as the fabrication method allows the aspect ratio required to obtain the desired depth. The fabrication of the grooves may be established by micro milling. The microfluidic probe head 100 may be made of at least one of the following: silicon, glass, polymethyl methacrylate, PMMA, polydimethylsiloxane, PDMS, aluminum, stainless steel, ceramics and other polymers. Hence, the here proposed concept may allow a wide variety of different materials, all of which may be used for microfluidic devices.

More details and aspects are mentioned in connection with the embodiments described above or below. The embodiment shown in FIG. 1, and the following embodiments, may comprise one or more optional additional features corresponding to one or more aspects mentioned in connection with the proposed concept, or one or more of the embodiments described below (e.g., FIGS. 2-8).

Figure 2:
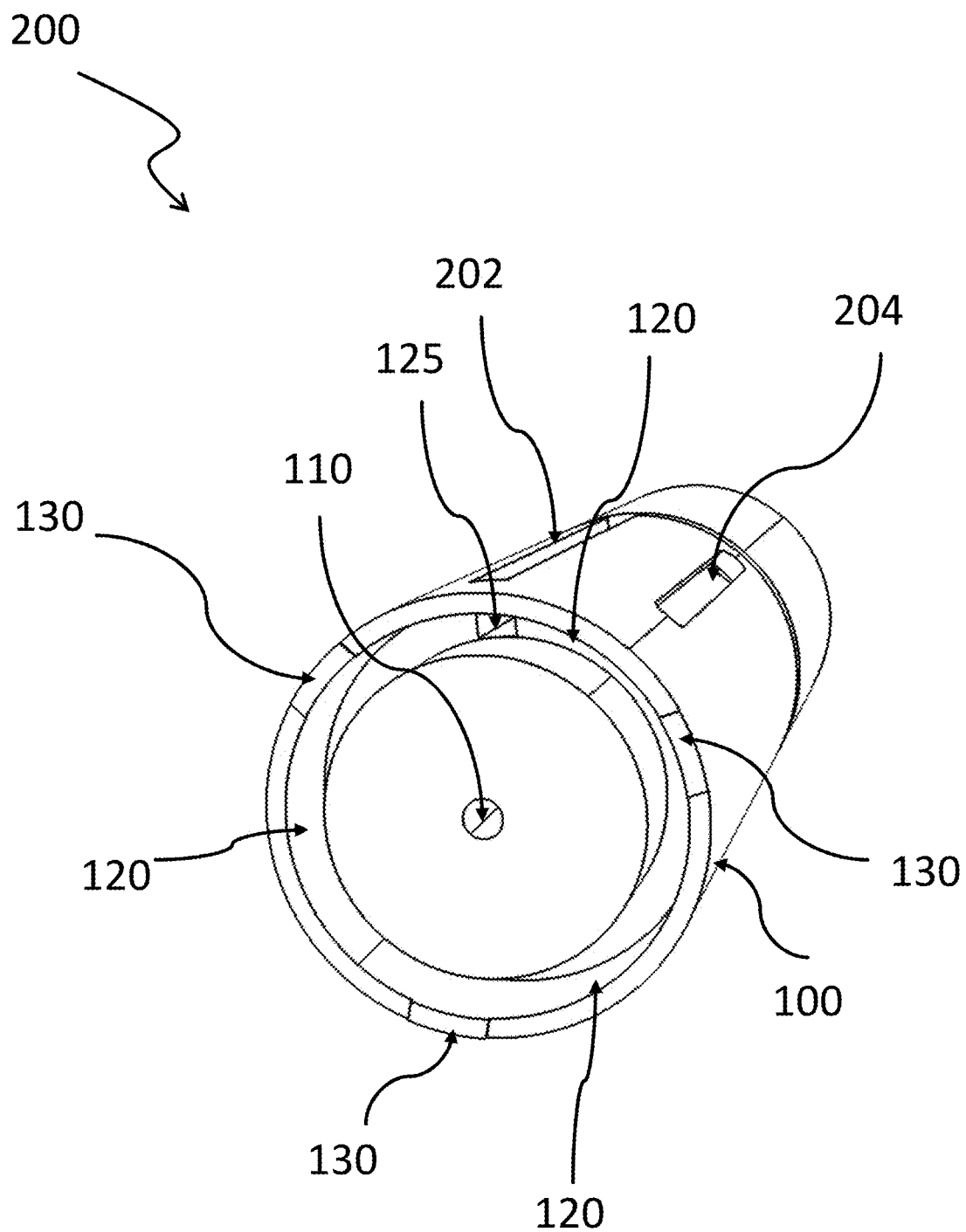
FIG. 2 shows a schematic illustration of an embodiment of a microfluidic probe.

FIG. 2 shows a schematic illustration of a microfluidic probe 200, according to an embodiment. The microfluidic probe 200 comprises the microfluidic probe head 100 with the specifications, as described above and below. The microfluidic probe head 100 in FIG. 2 comprises a shallow ring-shaped second aperture 120 with a single aspiration channel 125. The depth of the second aperture 120 may be larger than 1 mm (or 1.25 mm or 1.5 mm). For example, the depth and width ratio may be adjusted according to the description in FIG. 1. The first aperture 110 through which the fluid transported through the injection channel 110 enters the processing surface of the microfluidic probe head 100 may have a larger diameter in comparison to the single aspiration channel 125 or a similar diameter. The single aspiration channel 125 may be provided anywhere along the second aperture 120. In the case of a shallower depth of the second aperture, as described above with respect to FIG. 1, a plurality of aspiration channels 125 may be distributed on the periphery of the microfluidic probe head 100, in particular in the second aperture 120. If the aspiration channels are equally distributed around the injection channel 110, an equally and homogeneous liquid flow from the injection channel 110 to the aspiration channels can be achieved. It should be appreciated that any suitable number of aspiration channel(s) 125 are possible. It should be appreciated that the total cross section of the sum of the aspiration channels is equal or larger than the cross section of the injection channel 110 in order to discharge the probe head 100 from access liquid (or gas). Alternatively, a plurality of injection channels may be used. The cross section condition (see above) may then be applied accordingly.

As in microfluidic applications, due to imperfect sealing, air pockets or surface nucleation, bubbles may arise through the injection channel(s) or in the groove 120. Due to the hydrodynamic characteristics of this system, any bubble present will tend to be displaced inside the groove and stay at its bottom (if not aspirated by outlet channels, namely the aspiration channels). In certain embodiments, the groove 120 has been seen to be very robust to the presence of bubbles, provided that they do not fill 50% or more of the groove volume. The groove 120 can therefore act simultaneously as a flow distributor and a bubble trap, with no loss of aspiration operability.

Furthermore, the microfluidic probe 200 in FIG. 2 comprises a first recess 202 and a second recess 204 for connecting hoses or tubes via holes (not shown) in the far end of the microfluidic probe 200. The first recess 202 is provided for connecting an aspiration hose and the second recess 204 is provided for connecting an injecting hose at the far end of the of the microfluidic probe 200. This may reduce stress on the microfluidic probe 200 caused by drilling respective holes for the injection channel 110 and the aspiration channel 125. The outer side of the of the microfluidic probe 200 may be covered by a heat shrink tubing which may then close the open sides of the recesses 202 and 204 such that respective channels are built for aspiration and injection.

Figure 3:
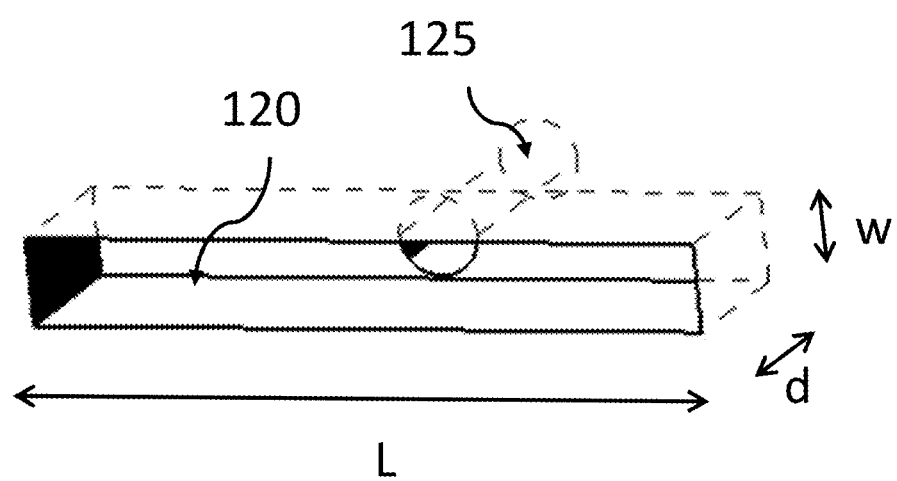
FIG. 3 shows a schematic illustration of a straight aperture of a microfluidic probe head with a corresponding aspiration channel, in an embodiment.

FIG. 3 shows a schematic illustration of a straight aperture 120 of a microfluidic probe head with a corresponding aspiration channel 125. FIG. 3 illustrates that the second aperture 120 in the figures above and below may also be straight. The straight aperture 120 may also have a similar depth and width relationship, as described with respect to FIG. 1. The straight aperture 120 may be arranged next to an injection channel of the microfluidic probe head (not shown in FIG. 3). The length of the straight aperture 120 may be larger than half a diameter of a processing surface of the microfluidic probe head. It is even possible to have two of these straight apertures 120 arranged at the processing surface of the microfluidic probe head. The arrangement of two of these straight apertures 120 may be point-wise symmetric around an injection channel (not shown in FIG. 3) of the microfluidic probe head.

At a microscale length-scale and laminar flow regime, the second aperture, as defined by a groove that is sufficiently deep, can be used to obtain a homogeneous distribution of aspirating/injecting velocities in its entire width and length from a single or few aspiration channels 125. A sufficient depth (d in FIG. 3) may be for example larger than 0.5 mm (or 0.75 mm or 1 mm or 1.25 mm or 1.5 mm or 1.75 mm or 2 mm). The width may then be defined in accordance with the formulas described above with respect to FIG. 1.

In certain embodiments, the length L of the aperture 120 is defined with regard to a size of the microfluidic probe head, for example in FIG. 1, or with regard to a size of the aspiration channel 125. In certain embodiments, the width w of the aperture 120 is larger than a diameter of the aspiration channel 125. In certain embodiments, the length L of the aperture 120 is 3 times (or 4 times or 5 times or 6 times or 7 times or 8 times or 9 times or 10 times) as large as the diameter of the aspiration channel 125 or the width w of the aperture 120. In certain embodiments, the length L of the aperture 120 is 0.5 times (or 0.6 times or 0.7 times) larger than a diameter of the processing surface of the microfluidic probe head (not shown in FIG. 3).

Figure 4A:
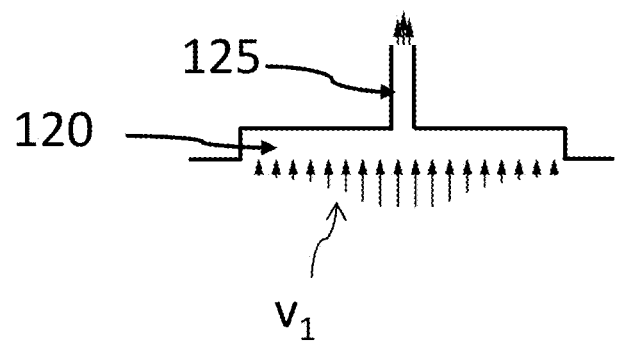
FIGS. 4a, 4b and 4c show schematic illustrations of an aperture of a microfluidic probe head with corresponding depths of the aperture, in an embodiment.
Figure 4B:
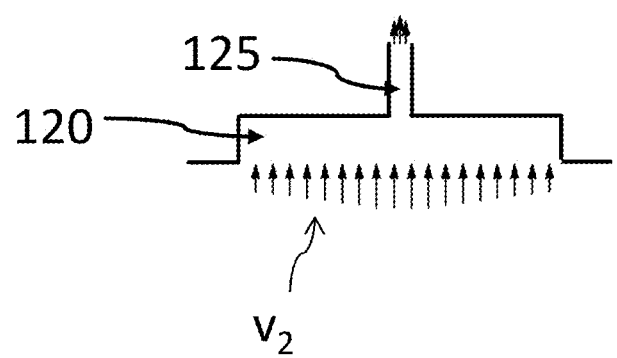
Figure 4C:
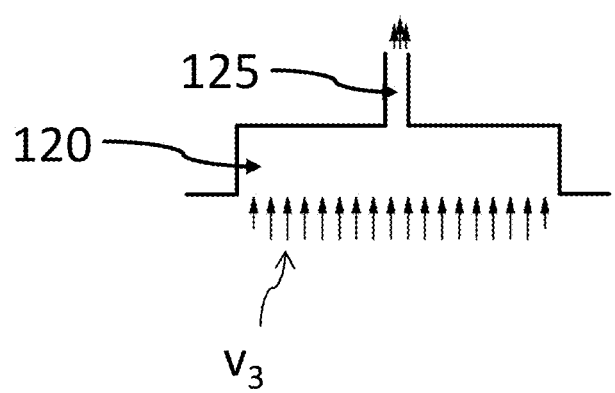

FIGS. 4a, 4b and 4c show schematic illustrations of an aperture of a microfluidic probe head with corresponding depths of the aperture, according to embodiments. The illustrations are given in a longitudinal section view. The distribution of flow velocities $v_1$, $v_2$ and $v_3$ in the vertical direction at the bottom of the groove 120 becomes homogeneous with a sufficient depth of the groove. The geometry (or the groove 120) may act as a flow velocity redistributor. For example, in FIG. 4a, the depth of the groove 120 is 0.5 mm, in FIG. 4b, the depth of the groove 120 is 1 mm, and in FIG. 4c, the depth of the groove 120 is 1.5 mm.

In FIGS. 4a, 4b and 4c, the length of the respective arrows below the aperture should illustrate a respective velocity. The longer the length of the respective arrow, the higher the velocity. In FIG. 4a, the fluid flow velocity is higher in the middle of the aperture and becomes lower at sides of the aperture. The same applies to FIG. 4b, wherein the fluid flow velocity also smooths out to the sides of the aperture with a lower fluid flow velocity in the middle compared to FIG. 4a. In FIG. 4c, the fluid flow velocity is uniformly distributed over the whole aperture due to the depth of the aperture. Thus, adapting the depth of the aperture (deeper from FIGS. 4a to 4c) may lead to a uniform fluid flow velocity over the whole aperture.

Figure 5A:
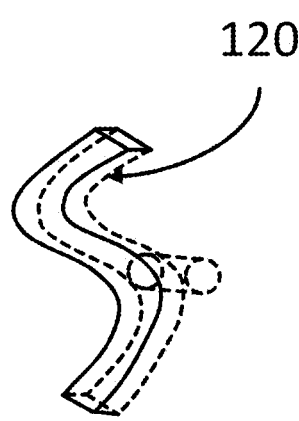
FIG. 5a shows a schematic illustration of an aperture of a microfluidic probe head forming a slot with an S-shaped curve, in an embodiment.
Figure 5B:
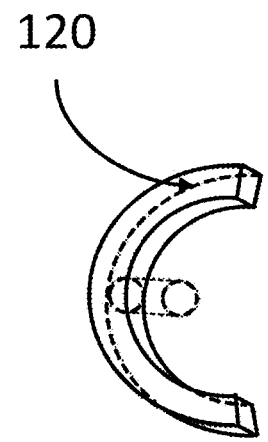
FIG. 5b shows a schematic illustration of an aperture of a microfluidic probe head forming a slot with a C-shaped curve, in an embodiment.

FIG. 5a shows a schematic illustration of an aperture of a microfluidic probe head forming a slot with an S-shaped curve, according to an embodiment. FIG. 5b shows a schematic illustration of an aperture of a microfluidic probe head forming a slot with a C-shaped curve.

Therefore, the second aperture 120 may be in the form of a linearly shaped groove. However, the groove is not limited to straight geometries. It can be shaped as a curve or form a full periphery (circumference).

Figure 5C:
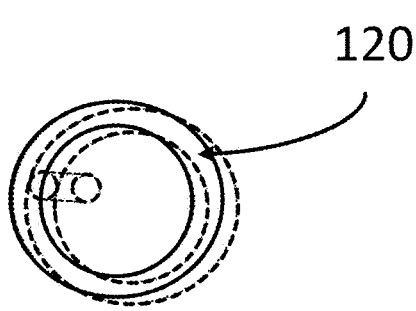
FIG. 5c shows a schematic illustration of an aperture of a microfluidic probe head forming a slot with a round shaped curve, in an embodiment.
Figure 5D:
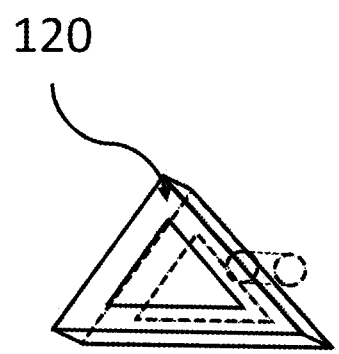
FIG. 5d shows a schematic illustration of an aperture of a microfluidic probe head forming a slot with a triangle shaped curve, in an embodiment.
Figure 5E:
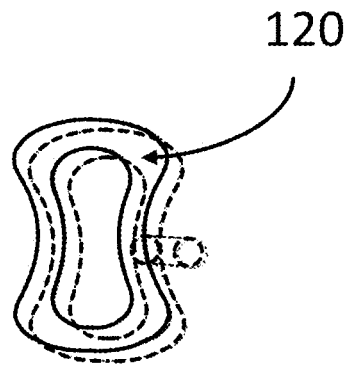
FIG. 5e shows a schematic illustration of an aperture of a microfluidic probe head forming a slot with a closed shaped curve being pressed together along one axis, in an embodiment.
Figure 5F:
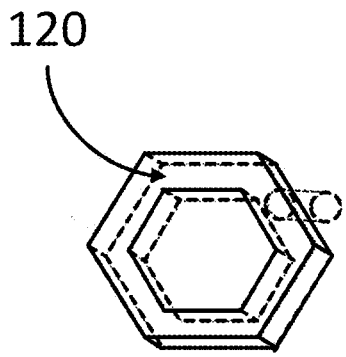
FIG. 5f shows a schematic illustration of an aperture of a microfluidic probe head forming a slot with a hexagon shaped curve, in an embodiment.

FIG. 5c shows a schematic illustration of an aperture for a microfluidic probe head forming a slot with a round shaped curve, according to an embodiment. FIG. 5d shows a schematic illustration of an aperture of a microfluidic probe head forming a slot with a triangle shaped curve. FIG. 5e shows a schematic illustration of an aperture of a microfluidic probe head forming a slot with a closed shaped curve being pressed together along one axis. FIG. 5f shows a schematic illustration of an aperture of a microfluidic probe head forming a slot with a hexagon shaped curve.

Therefore, the second aperture 120 may be in the form of a closed-shaped loop. The microfluidic probe head may have an inert injection aperture 110 enclosed by the loop shaped second aperture 120. In this case the second aperture 120 can act as a uniform aspirator which, combined with a central injector, can serve to obtain very stable flow confinements of any desired shape.

Figure 6:
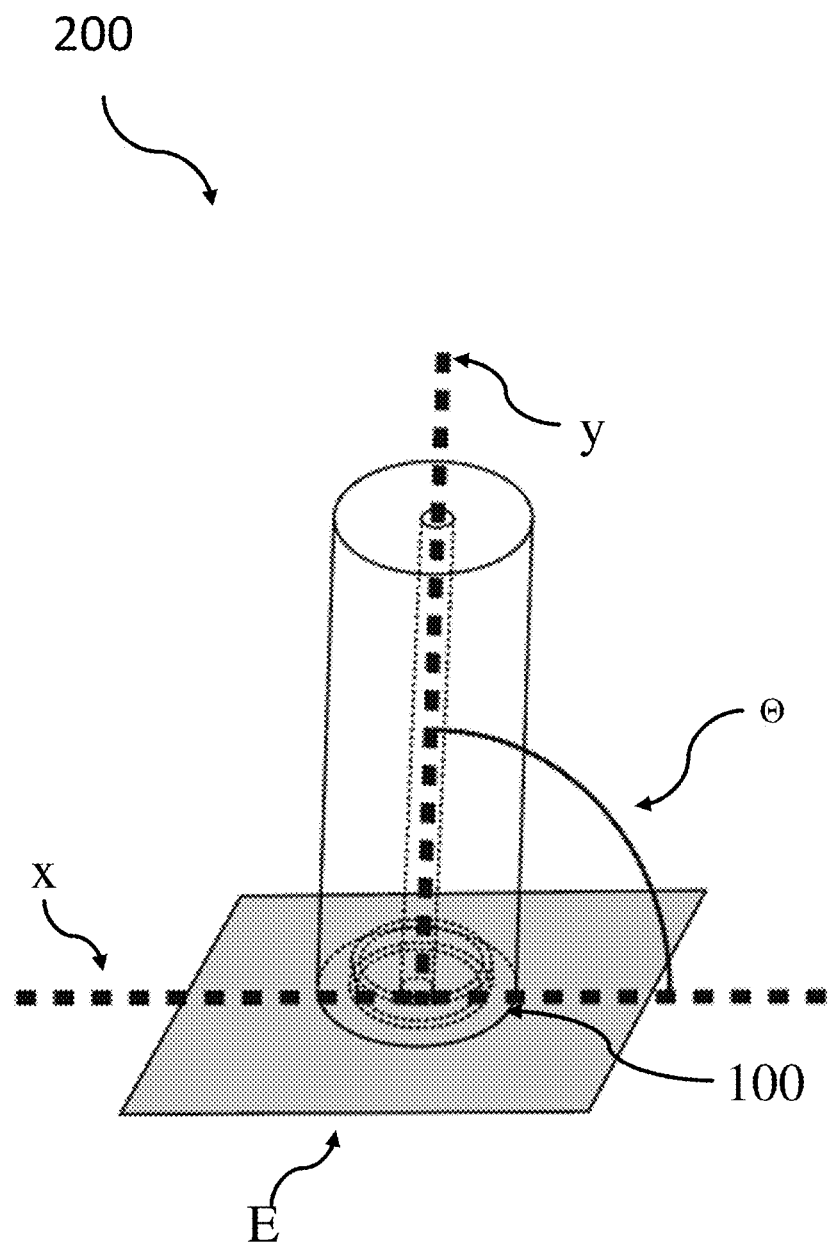
FIG. 6 shows a schematic illustration of a microfluidic probe in a tilted position, in an embodiment.

FIG. 6 shows a schematic illustration of a microfluidic probe 200 with its microfluidic probe head 100 in a tilted position, according to an embodiment. In the presence of immersion liquid, a hydrodynamic wall is formed between the inner confinement and the outside environment (not shown that the microfluidic probe head 100 is dipped into a liquid in FIG. 6). This hydrodynamic wall is very stable, irrespective of height. As a consequence, the confinement is not affected by a not perfectly perpendicular alignment between the main axis x of the microfluidic probe 200 and the surface (misalignment (90°-Θ) in vertical direction y of the microfluidic probe 200—not parallel to the surface/substrate E). Thus, no overflow of the confined liquid into immersion liquid area may result therefrom.

Figure 7:
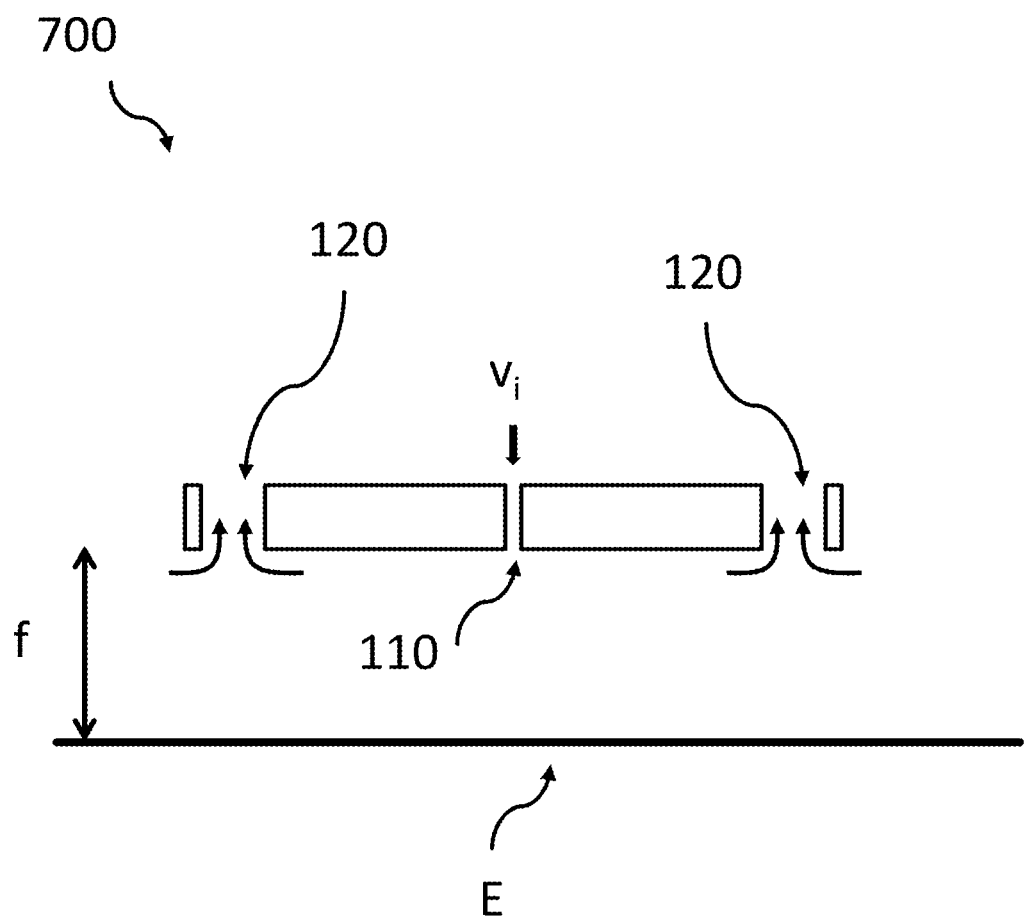
FIG. 7 shows a schematic illustration of a microfluidic probe head with injection channel and aspiration channels in relation to a surface, in an embodiment.

FIG. 7 shows a schematic illustration of a cross section of a microfluidic probe head 700 with injection channel 110 and aperture 120 in relation to a surface. The distance f between the microfluidic probe head 100 and the surface to be processed may be fixed by a spacer, as described above, or may be controllable by a separate robotic control unit (not shown).

Because of its symmetry, the confinement is stable at large gaps f between surface E and the processing surface of the microfluidic probe head 100 (for example larger than 1 mm). In vertical use, the microfluidic probe head 100 may be used at distances f being in a range between 25 µm and 2 mm. The flow velocity (illustrated as vertical arrow $v_i$) in the aperture 120 may be around $v_{aspiration}=25$ µL/min, and the flow velocity in the injection channel 110 may be around $v_{injection}=5$ µL/min. The flow into the aperture 120 is shown as curved lines going upwards.

Directly below the groove, a low flow velocity area is formed. Heavy enough particles for which the vertical flow lift is inferior to its gravitational weight may deposit in this area while smaller particles will be aspirated.

By tuning the flow velocities in dependence of the aspiration profile, it is possible to obtain the deposition of particles in a given shape (shape of aspiration structure) over a selected mass threshold. The particles may be at least one of magnetic beads, latex beads or cells. Low flow velocity areas may be defined at the aperture 120. High flow velocity areas may be defined at the first aperture 110. This may be achieved by providing an injection channel 110 being smaller than aspiration channels (not shown) guiding away from the aperture.

Figure 8:
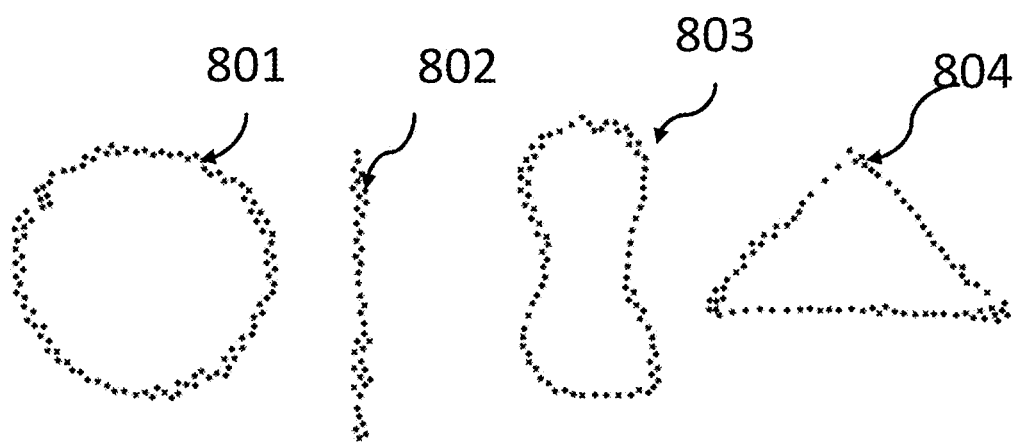
FIG. 8 shows a schematic illustration of cell patterns which can be obtained with different slot patterns, in an embodiment.

FIG. 8 shows a schematic illustration of cell patterns 801, 802, 803 and 804 which can be obtained with different slot patterns/groove geometries. These cell patterns 801, 802, 803 and 804 may be directly defined by or complement to the second aperture of the microfluidic probe head, as described above. These cell patterns 801, 802, 803 and 804 may then be provided below the microfluidic probe head when in use.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The terminology used herein is for the purpose of describing particular embodiments only and is not intended to be limiting. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

What is claimed is:

1. A microfluidic probe head comprising:
   a processing surface having a first aperture and a second aperture;
   a fluid injection channel leading to the first aperture; and
   a first fluid aspiration channel leading to the second aperture, wherein the second aperture is a slot formed into the processing surface in a closed-shaped loop encircling the first aperture.

2. The microfluidic probe head according to claim 1, wherein the second aperture is positioned around the first aperture.

3. The microfluidic probe head according to claim 1, wherein the second aperture is positioned apart from the first aperture.

4. The microfluidic probe head according to claim 1, wherein the first aperture is positioned at a center of the processing surface.

5. The microfluidic probe head according to claim 1, wherein the second aperture has a first dimension and a second dimension.

6. The microfluidic probe head according to claim 1, wherein the second aperture is point-wise symmetric around the first aperture.

7. The microfluidic probe head according to claim 1, wherein the second aperture is axis-symmetric to an axis running through the first aperture.

8. The microfluidic probe head according to claim 1, wherein the second aperture is a circular-shaped slot, rectangular-shaped slot or a triangular-shaped slot.

9. The microfluidic probe head according to claim 5, wherein the first dimension is a depth of the slot, and wherein the second dimension is a width of the slot.

10. The microfluidic probe head according to claim 5, wherein the first dimension has a size larger than three times the second dimension.

11. The microfluidic probe head according to claim 5, further comprising a second aspiration channel leading to the second aperture, wherein the first dimension has a size between three times the second dimension and twice the second dimension.

12. The microfluidic probe head according to claim 11, further comprising a third aspiration channel, wherein the first dimension has a size between the second dimension and twice the second dimension.

13. The microfluidic probe head according to claim 12, wherein at least two out of the first, second and third aspiration channels are point-wise symmetrically arranged with respect to the fluid injection channel.

14. The microfluidic probe head according to claim 12, wherein at least one of the first aspiration channel, the second aspiration channel and the third aspiration channel begins at a bottom of the second aperture.

15. The microfluidic probe head according to claim 1, wherein the fluid injection channel begins at the processing surface.

16. The microfluidic probe head according to claim 12, wherein respective diameters of the first aspiration channel, the second aspiration channel and the third aspiration channel are at least substantially the same.

17. The microfluidic probe head according to claim 12, wherein a respective diameter of the fluid injection channel is smaller than a sum of respective diameters of the first aspiration channel, the second aspiration channel and/or the third aspiration channel.

18. The microfluidic probe head according to claim 1, further comprising at least two protrusions at an edge of the processing surface, and wherein the at least two protrusions are configured to provide a predetermined distance from a surface on which the microfluidic head is applied.

19. The microfluidic probe head according to claim 18, wherein the at least two protrusions define at least part of an outer dimension of the processing surface.

20. A microfluidic probe comprising:
a microfluidic probe head including
    a processing surface having a first aperture and a second aperture,
    a fluid injection channel leading to the first aperture, and
    a first fluid aspiration channel leading to the second aperture, wherein the second aperture is a slot formed into the processing surface in a closed-shaped loop encircling the first aperture.

* * * * *